US006737082B1

(12) United States Patent
Picornell Darder

(10) Patent No.: US 6,737,082 B1
(45) Date of Patent: May 18, 2004

(54) PHARMACEUTICAL ORAL PREPARATION OF A COMPOUND HAVING AN ANTIFUNGIC ACTIVITY, AND PREPARATION METHOD

(75) Inventor: Carlos Picornell Darder, Madrid (ES)

(73) Assignee: Liconsa Liberacion Controlada de Sustancias Activas, S.A., Madrid (ES)

( * ) Notice: Subject to any disclaimer, the term of this patent is extended or adjusted under 35 U.S.C. 154(b) by 0 days.

(21) Appl. No.: 09/744,322

(22) PCT Filed: Jul. 20, 1999

(86) PCT No.: PCT/ES99/00230

§ 371 (c)(1),
(2), (4) Date: Mar. 22, 2001

(87) PCT Pub. No.: WO98/00116

PCT Pub. Date: Jan. 8, 1998

(30) Foreign Application Priority Data

Jul. 21, 1998 (ES) ................................................ 9801539

(51) Int. Cl.$^7$ ........................ A61K 9/12; A61K 31/495
(52) U.S. Cl. ........................ 424/494; 424/490; 424/491; 424/492; 424/493; 424/494; 424/495; 424/496; 424/497; 424/498; 514/777; 514/252.01
(58) Field of Search ................................. 424/490–498; 514/777, 252.01

(56) References Cited

U.S. PATENT DOCUMENTS 5,629,017 A * 5/1997 Pozzi et al. .................. 424/476
5,633,015 A * 5/1997 Gilis et al. ................... 424/490
5,834,023 A * 11/1998 Chen .......................... 424/497

FOREIGN PATENT DOCUMENTS

WO 9800116 1/1998
WO 9842318 10/1998

* cited by examiner

Primary Examiner—Russell Travers
Assistant Examiner—Shahnam Sharareh
(74) Attorney, Agent, or Firm—Steinberg & Raskin, P.C.

(57) ABSTRACT

It comprises a compound having antifungal activity as active principle, an inert core and a coating including said active principle, and is characterized in that said inert core has a particle size comprised between 50 and 600 $\mu$m, and in that said coating comprises a single layer obtained by spraying, on said inert core, a solution comprising a compound having antifungal activity, a hydrophilic polymer and a non-ionic surfactant.

The method consists in carrying out a coating, comprising a single layer, of the inert cores having a size between 50 and 600 $\mu$m, by means of the spraying of a solution composed by the antifungal agent, the hydrophilic polymer and the non-ionic surfactant, at a constant coating speed throughout the whole process; and a single drying step of said coating in the same apparatus.

17 Claims, No Drawings

PHARMACEUTICAL ORAL PREPARATION OF A COMPOUND HAVING AN ANTIFUNGIC ACTIVITY, AND PREPARATION METHOD

This application is a 371 of PCT/ES99/00230 filed in Jul. 2, 1999, which claims priority to Spanish Application 9801539 filed Jul. 21, 1998.

FIELD OF THE INVENTION

The present invention relates to an oral pharmaceutical composition comprising a compound having antifungal activity and in which the problems of low bioavailability, due to the poor solubility of antifungal compounds in an aqueous medium, are solved.

The present invention also relates to a method for obtaining said oral pharmaceutical composition that has advantages over conventional methods.

BACKGROUND OF THE INVENTION

The problems of solubility associated to the chemical structures of azoles such as itraconazole and saperconazole, compounds respectively described in U.S. Pat. Nos. 4,267,179 and 4,916,134, try to be solved by preparing different pharmaceutical forms on the base of the different administration methods.

It is known that the solubility of a compound can increase when it is added to an hydrophilic polymer and apply the mixture on an inert core. A formulation is obtained that improves remarkably the bioavailability of the compound.

In patent EP 658103 (published in Spain as ES 2097536 T3) pellets of itraconazole and saperconazole prepared on the basis of this technology. It discloses the preparation of a solution in ethanol and methylene chloride of the antifungal compound and the hydrophilic polymer hydroxypropylmethylcellulose (HPMC) which is sprayed in a fluidized bed on inert cores having a size between 600 and 700 $\mu$m. Once the spraying process is finished, the beads are dried in the same apparatus during ten minutes at a temperature of 50–55° C., but thereafter they must be introduced in a vacuum drier for about 36 hours at a temperature of 80° C. The dry cores are sieved and are subjected to a second coating process in order to form a second layer with a solution of polyethylene glycol 20000 (PEG 20000) in a fluidized bed. When the process is finished, the beads are dried in the apparatus for 10 minutes at 50–55° C. and then dry air at 20–25° C. is supplied to them during 5–15 minutes. When the drying process is finished, they are stored in suitable containers.

EP 658103 teaches that the second coating layer with PEG 20000, which is a sealing coating layer, is applied in order to prevent pellets from adhering, and that it is necessary to have inert cores of a size between 600 and 700 $\mu$m in order to avoid drying problems and pellet aggregation. According to EP 658103, inert cores having a larger size involve a smaller specific surface, whereby the coating layers need to be very thick and thus difficult to dry, while if the inert core size is too small it gives rise to a thin coating layer, easy to dry but that can undergo agglomeration phenomena during the coating step.

DESCRIPTION OF THE INVENTION

The present invention provides an oral pharmaceutical formulation and a working method that allow to solve the problems of solubility, drying and bioavailability of pellets of antifungal compounds.

The new formulation object of the present invention is characterized in that it consists of spherical beads comprising an inert core coated with a single layer of active charge comprising an antifungal compound. The process of coating the inert cores is carried out by spraying a solution of antifungal compound.

The oral pharmaceutical composition of the present invention comprises:

a/ an inert core
b/ a soluble active layer obtained from a solution comprising:
   an active principle having antifungal activity
   an hydrophilic polymer
   a non-ionic surfactant.

The active principles having antifungal activity included in the scope of the present invention are itraconazole, (±)-cis-4-[4-[4-[4-[[2-(2,4-dichlorophenyl)-2-(1H-1,2,4-triazol-1-yl-methyl)-1,3-dioxolan-4-yl]methoxy]phenyl]-1-piperazinyl]phenyl]-2,4-dihydro-2-(1-methylpropyl)-3H-1,2,4-triazol-3-one, and saperconazole, (±)-cis-4-[4-[4-[[2-(2,4-difluorophenyl)-2-(1H-1,2,4-triazol-1-yl-methyl)-1,3-dioxolan-4-yl]methoxy]phenyl]-1-piperazinyl]phenyl]-2,4-dihydro-2-(1-methylpropyl)-3H-1,2,4-triazol-3-one.

The inert cores are neutral spherical microbeads which can have in their composition one or more of the following substances: sorbitol, mannitol, saccharose, starch, microcrystalline cellulose, lactose, glucose, trehalose, maltitol and fructose. Their size is comprised between 50–600 $\mu$m, preferably between 500–600 $\mu$m.

In the present invention, the solution to be sprayed on inert cores is formed by the active principle having antifungal activity, dissolved in a mixture of organic solvents formed by ethanol and methylene chloride, in which the hydrophilic polymer is dissolved, and a surfactant.

The hydrophilic polymer can be HPMC, hydroxypropylcellulose (HPC), polyvinyl pyrrolidone (PVP), methacrylates, etc. The weight to weight ratio (w/w) between the antifungal agent and the polymer is in the range [(1:1)–(1:3)].

The non-ionic surfactant can be propylene glycol esters, glycerol esters, (mono-di-tri-) acetylated sorbitan, (mono, di-tri) acetylated saccharose, polyoxyethylene sorbitan esters of fatty acids, polyoxyethylene alkyl ethers of fatty chain, polyoxyethylene-polyoxypropylene copolymers. etc. The weight to weight ratio between the antifungal agent and the surfactant lies within the range [(1.5:1)–(29:1)].

Another object of the present invention is a method for manufacturing the Galenic formulations of the invention.

In the following the method is described, paying special attention to the proportions of each component and the methodology used.

In a stainless steel tank of suitable size, ethanol and methylene chloride (65:35) (w/w) is mixed. The antifungal compound (2.8%–5.0%) (w/w), the hydrophilic polymer (3.5%–6.3%) (w/w) and the surfactant (0.2%–2.0%) (w/w) are added.

Thereafter the coating solution is sprayed to obtain a single layer on the neutral pellets having a size comprised between 50 and 600 $\mu$m, preferably 500–600 $\mu$m, in a fluidized bed. During the whole process the spraying speed is constant and the temperature is maintained at 45° C.

When the coating step is finished, the pellets are kept in the apparatus for 15 minutes at a temperature of 45° C., this being the last drying step.

This technology allows to work with inert cores of a size between 50 and 600 $\mu$m, which is smaller than that claimed in EP 658103 and which favours the coating process due to the increase of specific surface; surprisingly, this size does not give rise to any agglomeration problem, and further the layer of PEG 20000 sealing coating is not necessary, because the incorporation of the non-ionic surfactant surprisingly prevents particle agglomeration.

With the present invention the cost of the process is reduced by a reduction in time and in use of the appartus, and at the same time the final drying of the beads is favoured, thus minimizing the risk of non fulfillment of the Proper Manufacturing Standards.

The present invention uses a fluidized bed in which the coating process is carried out. It is not necessary to use a second apparatus to dry the coated beads: on the contrary, a short drying step (15 minutes at 45° C.), carried out in the same apparatus after completing the coating step of the single layer, is sufficient. Thus not only is the processing time lowered with respect to that of EP 658103, because the pellets or beads do not need to be placed in a vacuum drier: at the same time the step of subjecting them to extreme temperatures of 80° C. during 36 hours is avoided.

During the spraying process, the temperature to which the cores are subjected is 45° C., lower than the working temperature in EP 658103, and this is also a positive factor for controlling the chemical stability of the active principle and for avoiding the drawback, already commented in EP 658103, that high temperatures may accelerate drying of the beads, with the risk of formation of layers that are non-uniform and have high porosity.

During the coating process, the spraying speed is a factor to be considered in order to obtain a higher efficiency in the process. In EP 658103 it is recommended to start with a low speed that is gradually increased along the process; it is even mentioned that a speed too high can cause an excessive moistening of the beads, resulting in agglomeration phenomena. On the contrary, if the speed is low product losses can occur due to drying of the spray itself. In EP 658103 the spraying speed at the beginning of the coating, for the obtention of the first layer, is about 600–700 g/min, and it is raised to 800 g/min once 30% of the coating solution has been consumed. This range of speeds is higher than those used in the present invention. The coating speed of the present invention is lower and is maintained constant throughout the whole process.

In the present invention the technology described in EP 658103 has been improved, since work is performed with inert cores of smaller size than those described in EP 658103, without causing agglomeration of the beads. On the other hand, spraying at lower speed is achieved with no product losses, and the drying of the final beads is carried out at lower working temperatures and reducing the drying process practically to the loading time.

The use of a single apparatus in which both the coating step, comprising only one layer, and the drying, allows for another advantage not only in cost but also in processing time, and this in its turn involves less handling of the final bead, with improvements of its chemical and physical integrity.

EXAMPLE 18.60 kg of methylene chloride and 10.00 kg of ethanol are mixed in a stainless steel container; then 0.98 kg of itraconazole, 1.32 kg of hydroxypropylmethylcellulose and 0.39 kg of poloxamer are introduced.

In the fluidized bed are introduced 2 kg of inert cores composed of saccharose (62.5%–91.5%) and starch (37.5%–8.5%), having a size of 500–600 $\mu$m, and they are coated with the solution previously prepared, at a spraying speed of 30 g/min and at a product temperature of 45° C. Once the coating step is finished, the charged cores are dried in the same apparatus during 15 minutes at 45° C.

The present invention has been described herein with reference to preferred embodiments of the invention however the description provided herein is for illustrative purposes and should not be considered to be exhaustive. It is understood that modifications and variations of the above describe preferred embodiments are possible without departing from the spirit or scope of the present invention.

What is claimed is:

1. An oral pharmaceutical composition in the form of a pellet, comprising:
    a compound having antifungal activity selected from the group consisting of itraconazole and saperconazole as an active principle,
    an inert core and
    a coating including said active principle, wherein said inert core has a particle size between about 50 and 600 $\mu$m, and wherein said coating comprises a single layer obtained by spraying, on said inert core, a solution comprising a compound having antifungal activity, a hydrophilic polymer and a non-ionic surfactant.

2. An oral pharmaceutical composition as claimed in claim 1, wherein said inert core has a particle size between about 500 and 600 $\mu$m.

3. An oral pharmaceutical composition as claimed in claim 1, wherein said hydrophilic polymer is selected from the group consisting of hydroxypropylmethylcellulose (HPMC), hydroxypropylcellulose (HPC), polyvinyl pyrrolidone (PVP) and methacrylates.

4. An oral pharmaceutical composition as claimed in claim 1, wherein said non-ionic surfactant is selected from the group consisting of propylene glycol esters, glycerol esters, (mono-di-tri-)acetylated sorbitan, (mono, di-tri) acetylated saccharose, polyoxyethylene sorbitan esters of fatty acids, polyoxyethylene alkyl ethers of fatty chain, and polyoxyethylene-polyoxypropylene copolymers.

5. An oral pharmaceutical composition as claimed in claim 1:
    wherein the hydrophilic polymer is present in about 25% to 60% by weight,
    wherein the non-ionic surfactant is present in about 1% to 15% by weight,
    wherein said antifungal compound is present in about 19% to 30% by weight, and
    wherein the inert core in the final pellet is present in about 10% to 45% by weight.

6. An oral pharmaceutical composition as claimed in claim 1, wherein the weight to weight ratio between the antifungal compound and hydrophilic polymer is from about 1:1 to 1:3 and between the antifungal compound and the surfactant is from about 1.5:1 to 29:1.

7. A method for obtaining an oral pharmaceutical composition as claimed in claim 1, comprising the steps of:
    spraying a coating, comprising a single layer, on an inert core having a size between about 50 and 600 $\mu$m, of a solution comprising an antifungal agent, a hydrophilic polymer and a non-ionic surfactant, at a constant coating speed throughout the whole method; and
    drying said coating.

8. An oral pharmaceutical composition as claimed in claim 1, wherein the hydrophilic polymer is present in about 27% to 55% by weight.

9. An oral pharmaceutical composition as claimed in claim 1, wherein the non-ionic surfactant is present in about 3% to 10% by weight.

10. An oral pharmaceutical composition as claimed in claim 1, wherein said antifungal compound is present in about 20% to 25% by weight.

11. An oral pharmaceutical composition as claimed in claim 1, wherein the inert core in the final pellet is present in about 15% to 43% by weight.

12. A pellet form oral pharmaceutical composition, comprising:

an inert core, having a particle size between 50 and 600 μm and a single coating layer having an active principle including an antifungal compound selected from the group consisting of itraconazole and saperconazole incorporated therewith, a hydrophilic polymer and a non-ionic surfactant sprayed onto said inert core.

13. The pellet form oral pharmaceutical composition according to claim 12, wherein said particle size of said inert core is between about 500 and 600 μm.

14. The pellet form oral pharmaceutical composition according to claim 12, wherein said hydrophilic polymer is selected from the group consisting of hydroxypropylmethylcellulose (HPMC), hydroxypropylcellulose (HPC), polyvinyl pyrrolidone (PVP) and methacrylates.

15. The pellet form oral pharmaceutical composition according to claim 12, wherein said non-ionic surfactant is selected from the group consisting of propylene glycol esters, glycerol esters, (mono-di-tri-)acetylated sorbitan, (mono, di-tri)acetylated saccharose, polyoxyethylene sorbitan esters of fatty acids, polyoxyethylene alkyl ethers of fatty chain, and polyoxyethylenepolyoxypropylene copolymers.

16. The pellet form oral pharmaceutical composition according to claim 12, wherein the hydrophilic polymer is present in about 25% to 60% by weight;

wherein the non-ionic surfactant is present in about 1% to 15% by weight;

wherein said antifungal compound is present in about 19% to 30% by weight; and wherein the inert core in the final pellet is present in about 10% to 45% by weight.

17. The pellet form oral pharmaceutical composition according to claim 12, wherein the weight to weight ratio between the antifungal compound and hydrophilic polymer is from about 1:1 to 1:3, and the weight to weight ratio between the antifungal compound and the surfactant is from about 1.5:1 to 29:1.

* * * * *

UNITED STATES PATENT AND TRADEMARK OFFICE
CERTIFICATE OF CORRECTION

PATENT NO. : 6,737,082 B1
DATED : May 18, 2004
INVENTOR(S) : Picornell Darde

It is certified that error appears in the above-identified patent and that said Letters Patent is hereby corrected as shown below:

Title page,
Item [87], PCT Pub: WO98/00116 should read -- WO00/04881
PCT Pub Date: Jan. 8, 1998 should read -- Feb. 3, 2000.

Signed and Sealed this

Third Day of August, 2004

JON W. DUDAS
*Acting Director of the United States Patent and Trademark Office*